US006500939B1

(12) United States Patent
Kato et al.

(10) Patent No.: US 6,500,939 B1
(45) Date of Patent: Dec. 31, 2002

(54) CDNAS CODING FOR HUMAN PROTEINS HAVING TRANSMEMBRANE DOMAINS

(75) Inventors: Seishi Kato, Sagamihara (JP); Shingo Sekine, Ageo (JP)

(73) Assignees: Sagami Chemical Research Center, Kanagawa (JP); Protogene, Inc., Tokyo (JP)

(*) Notice: Subject to any disclaimer, the term of this patent is extended or adjusted under 35 U.S.C. 154(b) by 0 days.

(21) Appl. No.: 09/529,157

(22) PCT Filed: Oct. 2, 1998

(86) PCT No.: PCT/JP98/04447

§ 371 (c)(1),
(2), (4) Date: Aug. 21, 2000

(87) PCT Pub. No.: WO99/18199

PCT Pub. Date: Apr. 15, 1999

(30) Foreign Application Priority Data

Oct. 8, 1997 (JP) .............................................. 9/276270

(51) Int. Cl.[7] ......................... C07H 21/02; C07H 21/04; C12N 1/00; C12N 15/00; C12N 5/08
(52) U.S. Cl. ................... 536/23.1; 435/325; 435/320.1; 435/366
(58) Field of Search .............................. 435/325, 320.1, 435/366, 23.1; 536/23.1

(56) References Cited

PUBLICATIONS

Michael Y. Galperin et al. Who's your neighbor? New computational approaches for functional genomics Nature Biotechnology vol. 18 Jun. 2000.*

Adams, M.D. et al., "EST13893 Testis tumor *Homo sapiens* cDNA 5' end similar to similar to protein transport protein SEC61, mRNA sequence," EMBL Database entry HSZZ0146, Acc. No. AA301007 (Apr. 1997).

Adams, M.D. et al., "EST100769 Pancreas tumor I *Homo sapiens* cDNA 5' end similar to similar to protein transport protein SEC61, mRNA sequence," EMBL Database entry HSZZ00740, Acc. No. AA295598 (Apr. 1997).

Adams, M.D. et al., "EST83699 Pituitary gland, subtracted (prolactin/growth hormone) II *Homo sapiens* cDNA 5' end similar to similar to protein transport protein SEC61, mRNA sequence," EMBL Database entry HSZZ7695, Acc. No. AA371870 (Apr. 1997).

Feng, Y. et al., "HIV–1 entry cofactor: functional cDNA cloning of a seven–transmembrane, G protein–coupled receptor," *Science*, May 10, 1996;272(5263):872–7.

Gorlich, D. et al., "A mammalian homolog of SEC61p and SECYp is associated with ribosomes and nascent polypeptides during translocation," *Cell*, Oct. 30, 1992;71(3):489–503.

Holloway, M.P. et al., "A hydrophobic domain of Ca2+– modulating cyclophilin ligand modulates calcium influx signaling in T lymphocytes," *J. Biol. Chem.*, Apr. 12, 1996;271(15):8549–52.

Kyte, J. et al., "A simple method for displaying the hydropathic character of a protein," *J. Mol. Biol.*, May 5, 1982;157(1):105–32.

Rommens, J.M. et al., "Identification of the cystic fibrosis gene: chromosome walking and jumping," *Science*, Sep. 8, 1989;245(4922):1059–65.

* cited by examiner

*Primary Examiner*—Remy Yucel
*Assistant Examiner*—Konstantina Katcheves
(74) *Attorney, Agent, or Firm*—Fitzpatrick, Cella, Harper & Scinto

(57) ABSTRACT

The invention provides cDNAs coding for human proteins having transmembrane domains and eucaryotic cells expressing said cDNAs. The cDNAs of the invention can be utilized as probes for the gene diagnosis and gene sources for the gene therapy. Furthermore, the cDNAs can be utilized for large-scale expression of said proteins. Cells, wherein these membrane protein genes are introduced and membrane proteins are expressed in large amounts, can be utilized for detection of the corresponding ligands, screening of novel low-molecular pharmaceuticals, and so on.

12 Claims, 2 Drawing Sheets

CDNAS CODING FOR HUMAN PROTEINS HAVING TRANSMEMBRANE DOMAINS

DESCRIPTION

1. Technical Field

The present invention relates to cDNAs coding for human proteins having transmembrane domains and eucaryotic cells expressing said cDNAs. The human cDNAs of the present invention can be utilized as probes for the gene diagnosis and gene sources for the gene therapy. Furthermore, the cDNAs can be utilized as gene sources for large-scale production of the proteins encoded by said cDNAs. Cells, wherein said cDNAs are expressed, can be utilized for detection of the corresponding ligands, screening of novel low-molecular pharmaceuticals, and so on.

2. Background Art

Membrane proteins play important roles, as signal receptors, ion channels, transporters, etc. in the material transportation and the information transmission which are mediated by the cell membrane. Examples thereof include receptors for a variety of cytokines, ion channels for the sodium ion, the potassium ion, the chloride ion, etc., transporters for saccharides and amino acids, and so on, where the genes of many of them have been cloned already.

It has been clarified that abnormalities of these membrane proteins are associated with a number of hitherto-cryptogenic diseases. For instance, a gene of a membrane protein having twelve transmembrane domains was identified as the gene responsible for cystic fibrosis [Rommens, J. M. et al., Science 245: 1059–1065 (1989)]. In addition, it has been clarified that several membrane proteins act as receptors when a virus infects the cells. For instance, HIV-1 is revealed to infect into the cells through mediation of a membrane protein fusin having a membrane protein on the T-cell membrane, a CD-4 antigen, and seven transmembrane domains [Feng, Y. et al., Science 272: 872–877 (1996)]. Therefore, discovery of a new membrane protein is anticipated to lead to elucidation of the causes of many diseases, so that isolation of a new gene coding for the membrane protein has been desired.

Heretofore, owing to difficulty in the purification, many membrane proteins have been isolated by an approach from the gene side. A general method is the so-called expression cloning which comprises transfection of a cDNA library in eucaryotic cells to express cDNAs and then detection of the cells expressing the target membrane protein on the membrane by an immunological technique using an antibody or a physiological technique on the change in the membrane permeability. However, this method is applicable only to cloning of a gene of a membrane protein with a known function.

In general, membrane proteins possess hydrophobic transmembrane domains inside the proteins, wherein, after synthesis thereof in the ribosome, these domains remain in the phospholipid membrane to be trapped in the membrane. Accordingly, the evidence of the cDNA for encoding the membrane protein is provided by determination of the whole base sequence of a full-length cDNA followed by detection of highly hydrophobic transmembrane domains in the amino acid sequence of the protein encoded by said cDNA.

DISCLOSURE OF INVENTION

The object of the present invention is to provide novel human proteins having transmembrane domains and DNAs coding for said proteins as well as transformation eucaryotic cells that are capable of expressing said cDNAs.

As the result of intensive studies, the present inventors have been successful in cloning of cDNAs coding for proteins having transmembrane domains from the human full-length cDNA bank, thereby completing the present invention. In other words, the present invention provides cDNAs coding for human proteins having transmembrane domains, exemplified by cDNAs containing either of the base sequences represented by SEQ ID NO:1 and SEQ ID NO:2, as well as transformation eucaryotic cells that are capable of expressing said cDNAs.

BEST MODE FOR CARRYING OUT THE INVENTION

Figure 1:
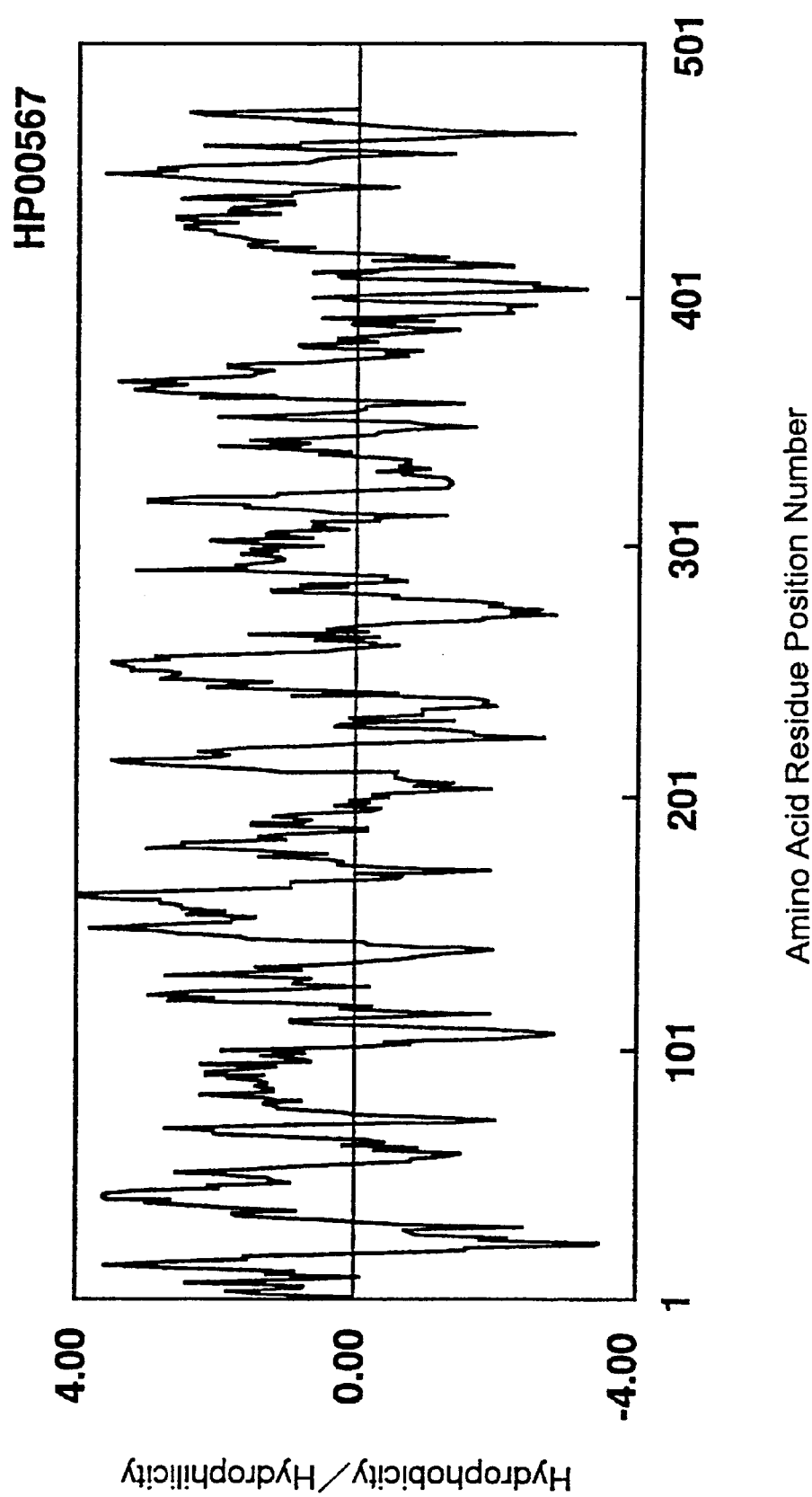
FIG. 1: A figure depicting the hydrophobicity/hydrophilicity profile of the protein encoded by clone HP00567.

The cDNAs of the present invention can be cloned, for example, from cDNA libraries of the human cell origin. These cDNA are synthesized by using as templates poly $(A)^+$ RNAs extracted from human cells. The human cells may be cells delivered from the human body, for example, by the operation or may be the culture cells. The cDNAs can be synthesized by using any method selected from the Okayama-Berg method [Okayama, H. and Berg, P., Mol. Cell. Biol. 2: 161–170 (1982)], the Gubler-Hoffman method [Gubler, U. and Hoffman, J. Gene 25: 263–269 (1983)], and so on, but it is preferred to use the capping method [Kato, S. et al., Gene 150: 243–250 (1994)], as exemplified in Examples, in order to obtain a full-length clone in an effective manner.

The primary selection of one of the cDNAs coding for the human proteins having transmembrane domains is carried out by sequencing of a partial base sequence of a cDNA clone selected at random from cDNA libraries, sequencing of the amino acid sequence encoded by the base sequence, and recognition of the presence or absence of a hydrophobic site in the resulting N-terminal amino acid sequence region. Next, the secondary selection is carried out by determination of the whole sequence by the sequencing and the protein expression by in vitro translation.

The cDNAs of the present invention are characterized by containing either of the base sequences represented by SEQ ID NO:1 and SEQ ID NO:2 or the base sequences represented by SEQ ID NO:3 and SEQ ID NO:4. Table 1 summarizes the clone number (HP number), the cells affording the cDNA, the total base number of the cDNA, and the number of the amino acid residues of the encoded protein, for each of the cDNAs.

TABLE 1

| SEQ ID NO: | HP No. | Cell | Number of Nucleotides | Number of amino acids |
|---|---|---|---|---|
| 1, 3 | HP00567 | PMA-U937 | 3570 | 476 |
| 2, 4 | HP00991 | stomach cancer | 819 | 185 |

Hereupon, the same clones as the cDNAs of the present invention can be easily obtained by screening of the cDNA libraries constructed from the human cell lines and human tissues utilized in the present invention by the use of an oligonucleotide probe synthesized on the basis of the cDNA base sequence described in either of SEQ ID NO:1 and SEQ ID NO:2.

In general, the polymorphism due to the individual difference is frequently observed in human genes. Accordingly, any cDNA that is subjected to insertion or deletion of one or plural nucleotides and/or substitution with other nucleotides in SEQ ID NO:1 to SEQ ID NO:4 shall come within the scope of the present invention.

The cDNAs of the present invention include cDNA fragments (more than 10 bp) containing any partial base sequence in the base sequences represented by SEQ ID NO:1 and SEQ ID NO:2 or in the base sequences represented by SEQ ID NO:3 and SEQ ID NO:4. Also, DNA fragments consisting of a sense chain and an anti-sense chain shall come within this scope. These DNA fragments can be utilized as the probes for the gene diagnosis.

In the case in which one of the cDNAs of the present invention is expressed in eucaryotic cells, the cDNA of the present invention can be expressed as a transmembrane protein on the cell-membrane surface, when the translation region of said cDNA is subjected to recombination to an expression vector for eucaryotic cells that has a promoter, a splicing region, a poly (A) addition site, etc., followed by introduction into the eucaryotic cells. The expression vector is exemplified by pKA1, pED6pdc2, pCDM8, pSVK3, pMSG, pSVL, pBK-CMV, pBK-RSV, EBV vector, pRS, pYES2, and so on. Examples of eucaryotic cells to be used in general include mammalian culture cells such as simian kidney cells COS7, Chinese hamster ovary cells CHO, etc., budding yeasts, fission yeasts, silkworm cells, *Xenopus laevis* egg cells, and so on, but any eucaryotic cells may be used, provided that they are capable of expressing the present cDNAs on the membrane surface. The expression vector can be introduced in the eucaryotic cells by methods known in the art such as the electroporation method, the potassium phosphate method, the liposome method, the DEAE-dextran method, and so on.

In addition to the activities and uses described above, the polynucleotides and proteins of the present invention may exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodiesusing DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Nutritional Uses

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

Cytokine and Cell Proliferation/Differentiation Activity

A protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/

G, M+ (preB M+), 2E8, RB5, DA1, 123, T1165, HT2, CTLL2, TF-1, Mo7e and CMK.

The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., J. Immunol. 149:3778–3783, 1992; Bowman et al., J. Immunol. 152: 1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J.E.e.a. Coligan eds. Vol 1 pp. 3.12.1–3.12.14, John Wiley and Sons, Toronto. 1994; and Measurement of mouse and human Interferon γ, Schreiber, R. D. In Current Protocols in Immunology. J.E.e.a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In Current Protocols in Immunology. J.E.e.a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6-Nordan, R. In Current Protocols in Immunology. J.E.e.a. Coligan eds. Vol 1 pp. 6.6.1–6.6.5, John Wiley and Sons, Toronto. 1991; Smith et al., Proc. Natl. Acad. Sci. U.S.A. 83:1857–1861, 1986; Measurement of human Interleukin 11—Bennett, F., Giannotti, J., Clark, S. C. and Turner, K. J. In Current Protocols in Immunology. J.E.e.a. Coligan eds. Vol 1 pp. 6.15.1 John Wiley and Sons, Toronto. 1991; Measurement of mouse and human Interleukin 9—Ciarletta, A., Giannotti, J., Clark,S. C. and Turner, K. J. In Current Protocols in Immunology. J.E.e.a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

Immune Stimulating or Suppressing Activity

A protein of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial orfungal infections, or may result from autoimmune disorders. More specifically, infectious diseases causes by viral, bacterial, fungal or other infection may be treatable using a protein of the present invention, including infections by HIV, hepatitis viruses, herpesviruses, mycobacteria, Leishmania spp., malaria spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as , for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. cad. Sci USA, 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the commoncold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class I $\alpha$ chain protein and $\beta_2$ microglobulin protein or an MHC class II$\alpha$ chain protein and an MHC class II$\beta$ chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Takai et al., J. Immunol. 140:508–512, 1988; Herrmann et al., Proc. Nati. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowman et al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In Current Protocols in Immunology. J. E.e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itohetal., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. USA 88:7548–7551, 1991.

Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lympho-hematopoiesis) include, without limitation, those described in: Methylcellulose colony forming assays, Freshney, M. G. In Culture of Hematopoietic Cells. R. I. Freshney, et al. eds. Vol pp. 265–268, Wiley-Liss, Inc., New York, N.Y. 1994; Hirayama et al., Proc. Natl. Acad. Sci. USA 89:5907–5911, 1992; Primitive hematopoietic colony forming cells with high proliferative potential, McNiece, I. K. and Briddell, R. A. In Culture of Hematopoietic Cells. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In Culture of Hematopoietic Cells. R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In Culture of Hematopoietic Cells. R. I. Freshney, et al. eds. Vol pp. 163–179, Wiley-Liss, Inc., New York, N.Y. 1994; Long term culture initiating cell assay, Sutherland, H. J. In Culture of Hematopoietic Cells. R. I. Freshney, et al. eds. Vol pp. 139–162, Wiley-Liss, Inc., New York, N.Y. 1994.

Tissue Growth Activity

A protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium ).

Assays for wound healing activity include, without limitation, those described in: Winter, Epidermal Wound Healing, pps. 71–112 (Maibach, HI and Rovee, DT, eds.), Year Book Medical Publishers, Inc., Chicago, as modified by Eaglstein and Mertz, J. Invest. Dermatol 71:382–84 (1978).

Activin/Inhibin Activity

A protein of the present invention may also exhibit activin- or inhibin-related activities. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin α family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-β group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986.

Chemotactic/Chemokinetic Activity

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Margulies, E. M. Shevach, W.Strober, Pub. Greene Publishing Associates and Wiley-Interscience (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25: 1744–1748; Gruber et al. J. of Immunol. 152:5860–5867, 1994; Johnston et al. J. of Immunol. 153: 1762–1768, 1994.

Hemostatic and Thrombolytic Activity

A protein of the invention may also exhibit hemostatic or thrombolytic activity. As a result,such a protein is expected to be useful in treatment of various coagulation disorders (includinghereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., J. Clin. Pharmacol. 26:131–140, 1986; Burdick et al., Thrombosis Res. 45:413–419, 1987; Humphrey et al., Fibrinolysis 5:71–79 (1991); Schaub, Prostaglandins 35:467–474, 1988.

Receptor/Ligand Activity

A protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selecting, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in:Current Protocols in Immunology, Ed by J. E. Coligan, A. M. Kruisbeek, D. H. Margulies, E. M. Shevach, W.Strober, Pub. Greene Publishing Associates and Wiley-Interscience (Chapter 7.28, Measurement of Cellular Adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169:149–160 1989; Stoltenborg et al., J. Immunol. Methods 175:59–68, 1994; Stitt et al., Cell 80:661–670, 1995.

Anti-Inflammatory Activity

Proteins of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of ytokines such as TNF or IL-1. Proteins of the invention may also be useful to treat anaphylaxis and hypersensitivity to an antigenic substance or material.

Tumor Inhibition Activity

In addition to the activities described above for immunological treatment or prevention of tumors, a protein of the invention may exhibit other anti-tumor activities. A protein may inhibit tumor growth directly or indirectly (such as, for example, via ADCC). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth Other Activities A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component (s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

EXAMPLES

The present invention is embodied in more detail by the following examples, but this embodiment is not intended to restrict the present invention. The basic operations and the enzyme reactions with regard to the DNA recombination are carried out according to the literature ["Molecular Cloning. A Laboratory Manual", Cold Spring Harbor Laboratory, 1989]. Unless otherwise stated, restrictive enzymes and a variety of modification enzymes to be used were those available from TAKARA SHUZO. The manufacturer's instructions were used for the buffer compositions as well as for the reaction conditions, in each of the enzyme reactions. The cDNA synthesis was carried out according to the literature [Kato, S. et al., Gene 150: 243–250 (1994)].

(1) Preparation of Poly(A)$^+$ RNA

The histiocyte lymphoma cell line U937 (ATCC CRL 1593) stimulated by phorbol ester and tissues of stomach cancer delivered by the operation were used for human cells to extract mRNAs. The cell line was incubated by a conventional procedure.

After about 1 g of the human cells was homogenized in 20 ml of a 5.5 M guanidinium thiocyanate solution, a total mRNA was prepared according to the literature [Okayama, H. et al., "Method in Enzymology", Vol. 164, Academic Press, 1987]. This was subjected to chromatography on oligo (dT)-cellulose column washed with a 20 mM Tris-hydrochloride buffer solution (pH 7.6), 0.5 M NaCl, and 1 mM EDTA to obtain a poly(A)$^+$ RNA according to the above-described literature.

(2) Construction of cDNA Library

Ten micrograms of the above-mentioned poly(A)$^+$ RNA were dissolved in a 100 mM Tris-hydrochloride buffer solution (pH 8), one unit of an RNase-free, bacterial alkaline phosphatase was added, and the reaction was run at 37° C. for one hour. After the reaction solution was subjected to phenol extraction, followed by ethanol precipitation, the resulting pellet was dissolved in a solution containing 50 mM sodium acetate (pH 6), 1 mM EDTA, 0.1% 2-mercaptoethanol, and 0.01% Triton X-100. Thereto was added one unit of a tobacco-origin acid pyrophosphatase (Epicentre Technologies) and a total 100 μl volume of the resulting mixture was reacted at 37° C. for one hour. After the reaction solution was subjected to phenol extraction, followed by ethanol precipitation, the resulting pellet was dissolved in water to obtain a solution of a decapped poly(A)$^+$ RNA.

The decapped poly(A)$^+$ RNA and 3 nmol of a chimeric DNA-RNA oligonucleotide (5'-dG-dG-dG-dG-dA-dA-dT-dT-dC-dG-dA-G-G-A-3') (SEQ ID NO:8) were dissolved in a solution containing 50 mM Tris-hydrochloride buffer solution (pH 7.5), 0.5 mM ATP, 5 mM MgCl$_2$, 10 mM 2-mercaptoethanol, and 25% polyethylene glycol, whereto was added 50 units of T4RNA ligase and a total 30 μl volume of the resulting mixture was reacted at 20° C. for 12 hours. After the reaction solution was subjected to phenol extraction, followed by ethanol precipitation, the resulting pellet was dissolved in water to obtain a chimeric-oligo-capped poly(A)$^+$ RNA.

After digestion of vector pKA1 (Japanese Patent Kokai Publication No. 1992-117292) developed by the present inventors With KpnI, about 60 dT tails were added using a terminal transferase. A vector primer to be used below was prepared by digestion of this product with EcoRV to remove a dT tail at one side.

After 6 μg of the previously-prepared chimeric-oligo-capped poly (A)$^+$ RNA was annealed with 1.2 μg of the vector primer, the resulting product was dissolved in a solution containing 50 mM Tris-hydrochloride buffer solution (pH 8.3), 75 mM KCl, 3 mM MgCl$_2$, 10 mM dithiothreitol, and 1.25 mM dNTP (dATP+dCTP+dGTP+dTTP), 200 units of a reverse transcriptase (GIBCO-BRL) were added, and the reaction in a total 20 μl volume was run at 42° C. for one hour. After the reaction solution was subjected to phenol extraction, followed by ethanol precipitation, the resulting pellet was dissolved in a solution containing 50 mM Tris-hydrochloride buffer solution (pH 7.5), 100 mM NaCl, 10 mM MgCl$_2$, and 1 mM dithiothreitol. Thereto were added 100 units of EcoRI and a total 20 μl volume of the resulting mixture was reacted at 37° C. for one hour. After the reaction solution was subjected to phenol extraction, followed by ethanol precipitation, the resulting pellet was dissolved in a solution containing 20 mM Tris-hydrochloride buffer solution (pH7.5), 100 mM KCl, 4mM MgCl$_2$, 10 mM (NH$_4$)$_2$SO$_4$, and 50 μg/ml of the bovine serum albumin. Thereto were added 60 units of an *Escherichia coli* DNA ligase and the resulting mixture was reacted at 16° C. for 16 hours. To the reaction solution were added 2 μl of 2 mM dNTP, 4 units of *Escherichia coli* DNA polymerase I, and 0.1 unit of *Escherichia coli* RNase H and the resulting mixture was reacted at 12° C. for one hour and then at 22° C. for one hour.

Next, the cDNA-synthesis reaction solution was used for transformation of *Escherichia coli* DH12S (GIBCO-BRL). The transformation was carried out by the electroporation method. A portion of the transformant was sprayed on the 2×YT agar culture medium containing 100 μg/ml ampicillin and the mixture was incubated at 37° C. overnight. A colony formed on the agar medium was picked up at random and inoculated on 2 ml of the 2×YT culture medium containing 100 μg/ml ampicillin. After incubation at 37° C. overnight, the culture mixture was centrifuged to separate the mycelia, from which a plasmid DNA was prepared by the alkaline lysis method. The plasmid DNA was subjected to double digestion with EcoRI and NotI, followed by 0.8% agarose gel electrophoresis, to determine the size of the cDNA insert. Furthermore, using the thus-obtained plasmid as a template, the sequence reaction was carried out by using an M13 universal primer labeled with a fluorescent dye and a Taq polymerase (a kit of Applied Biosystems) and then the product was examined with a fluorescent DNA sequencer (Applied Biosystems) to determine an about 400-bp base sequence at the 5'-terminus of the cDNA. The sequence data were filed as the homo/protein cDNA bank database.

(3) Selection of cDNAs Encoding Proteins Having Transmembrane Domains

A base sequence registered in the homo/protein cDNA bank was converted to three frames of amino acid sequences and the presence or absence of an open reading frame (ORF) beginning from the initiation codon was examined. Then, the selection was made for the presence of a signal sequence that is characteristic to a secretory protein at the N-terminus of the portion encoded by the ORF. These clones were sequenced from the both 5' and 3' directions by the use of the deletion method using exonuclease III to determine the whole base sequence. The hydrophobicity/hydrophilicity profiles were obtained for proteins encoded by the ORF by the Kyte-Doolittle method [Kyte, J. & Doolittle, R. F., J. Mol. Biol. 157: 105–132 (1982)] to examine the presence or absence of a hydrophobic region. In the case in which there is a hydrophobic region of a putative transmembrane domain in the amino acid sequence of an encoded protein, this protein was judged as a membrane protein.

(4) Protein Synthesis by In Vitro Translation

The plasmid vector bearing the cDNA of the present invention was used for in vitro transcription/translation with a $T_NT$ rabbit reticulocyte lysate kit (Promega). In this case, [$^{35}$S]methionine was added to label the expression product with a radioisotope. Each of the reactions was carried out according to the protocols attached to the kit. Two micrograms of the plasmid was reacted at 30° C. for 90 minutes in a total 25 μl volume of the reaction solution containing 12.5 μl of $T_NT$ rabbit reticulocyte lysate, 0.5 μl of a buffer solution (attached to kit), 2 μl of an amino acid mixture (methionine-free), 2 μl of [$^{35}$S]methionine (Amersham) (0.37 MBq/μl), 0.5 μl of T7RNA polymerase, and 20 U of RNasin. To 3 μl of the resulting reaction solution was added 2 μl of the SDS sampling buffer (125mM Tris-hydrochloric acid buffer, pH 6.8, 120 mM 2-mercaptoethanol, 2% SDS solution, 0.025% bromophenol blue, and 20% glycerol) and the resulting mixture was heated at 95° C. for 3 minutes and then subjected to SDS-polyacrylamide gel electrophoresis. The molecular weight of the translation product was determined by carrying out the autoradiograph.

(5) Expression by COS7

After *Escherichia coli* (host: JM109) bearing the expression vector of the present invention was incubated at 37° C. for 2 hours in 2 ml of the 2×YT culture medium containing 100 μg/ml of ampicillin, the helper phage M13KO7 (50 μl) was added and the incubation was continued at 37° C. overnight. A supernatant separated by centrifugation underwent precipitation with polyethylene glycol to obtain single-stranded phage particles. These particles were suspended in 100 μl of 1 mM Tris-0.1 mM EDTA, pH 8 (TE). Also, there were used as controls suspensions of single-stranded phage particles prepared in the same manner from pSSD3 and from the vector pKA1-UPA containing a full-length cDNA of urokinase [Yokoyama-Kobayashi, M. et al., Gene 163: 193–196 (1995)].

The culture cells originating from the simian kidney, COS7, were incubated at 37° C. in the presence of 5% $CO_2$ in the Dulbecco's modified Eagle's culture medium (DMEM) containing 10% fetal calf albumin. Into a 6-well plate (Nunc Inc., 3 cm in the well diameter) were inoculated 1×10$^5$ COS7 cells and incubation was carried out at 37° C. for 22 hours in the presence of 5% $CO_2$. After the culture medium was removed, the cell surface was washed with a phosphate buffer solution and then washed again with DMEM containing 50 mM Tris-hydrochloric acid (pH 7.5) (TDMEM). To the resulting cells was added a suspension of 1 μl of the single-stranded phage suspension, 0.6 ml of the DMEM culture medium, and 3 μl of TRANSFECTAM™ (IBF Inc.) and the resulting mixture was incubated at 37° C. for 3 hours in the presence of 5% $CO_2$. After the sample solution was removed, the cell surface was washed with TDMEM, 2 ml per well of DMEM containing 10% fetal calf albumin was added, and the incubation was carried out at 37° C. for 2 days in the presence of 5% $CO_2$. Furthermore, after the incubation was continued for one hour in the culture medium containing [$^{35}$S] cystine or [$^{35}$S]methionine, the cells were collected, dissolved, and then subjected to SDS-PAGE, whereby there was observed the presence of a band corresponding to the expression product of each protein. For instance, HP00991 produced a band of 18 kDa on the membrane fraction.

(6) Clone Examples

<HP00567> (Sequence Nos. 1, and 3)

Determination of the whole base sequence of the cDNA insert of clone HP00567 obtained from cDNA libraries of the human histiocyte lymphoma cell line U937 stimulated by phorbol ester revealed the structure consisting of a 119-bp 5'-nontranslation region, a 1431-bp ORF, and a 2020-bp 3'-nontranslation region. The ORF codes for a protein consisting of 476 amino acid residues and there existed at least nine transmembrane domains. FIG. 1 depicts the hydrophobicity/hydrophilicity profile, obtained by the Kyte-Doolittle method, of the present protein. In vitro translation resulted in the observation that there was not any band corresponding to the molecular weight of 52,264 predicted from the ORF and a smear translation product of a high molecular weight was formed.

The search of the protein data base by using the amino acid sequence of the present protein revealed that the protein was completely identical with the rat protein translocation protein Sec61 α subunit (SWISS-PROT Accession No. P38378). Furthermore, the search of the GenBank using the base sequences of the present cDNA has revealed the presence of sequences that possessed a homology of 90% or more (for example, Accession No. AA301007) in EST, but, since they are partial sequences, it can not be judged whether or not any of these sequences codes for the same protein as the protein of the present invention.

The rat protein translocation protein Sec61 α subunit plays an important role in protein translocation across the endoplasmic reticulum membrane [Gorlich, D. et al., Cell 71: 489–503 (1992)]. Accordingly, the present protein is a human homologue of the rat protein translocation protein Sec61 α subunit. The present cDNAs can be utilized for the diagnosis and treatment of diseases that are associated with the function insufficiency of endoplasmic reticulum.

<HP00991> (Sequence Nos. 2 and 4)

Figure 2:
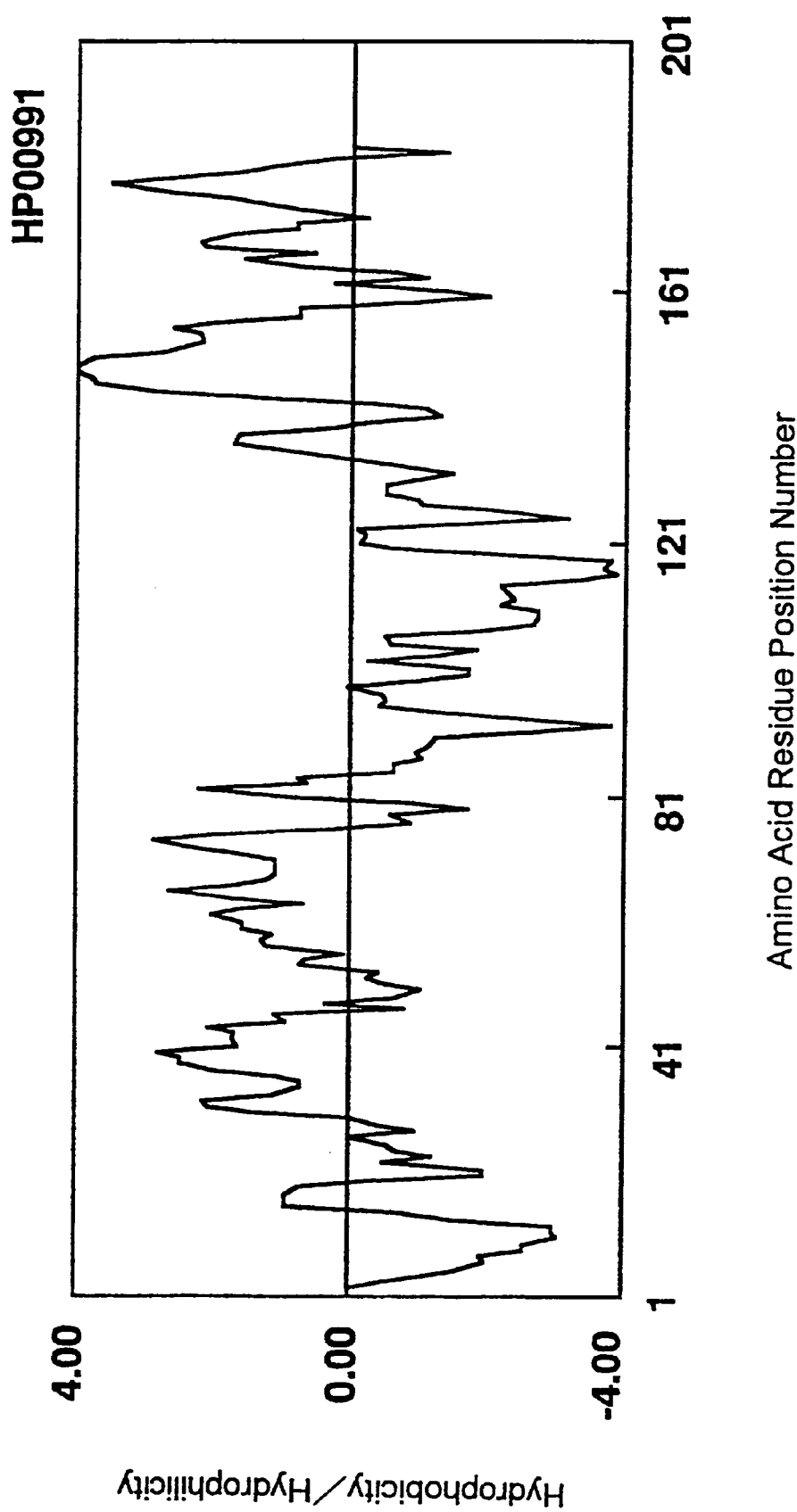
FIG. 2: A figure depicting the hydrophobicity/hydrophilicity profile of the protein encoded by clone HP00991.

Determination of the whole base sequence of the cDNA insert of clone HP00991 obtained from cDNA libraries of human stomach cancer revealed the structure consisting of a 65-bp 5'-nontranslation region, a 558-bp ORF, and a 196-bp 3'-nontranslation region. The ORF codes for a protein consisting of 185 amino acid residues and there existed four transmembrane domains. FIG. 2 depicts the hydrophobicity/hydrophilicity profile, obtained by the Kyte-Doolittle method, of the present protein. In vitro translation resulted in formation of a translation product of 21 kDa that was almost consistent with the molecular weight of 21,080 predicted from the ORF.

The search of the protein data base by using the amino acid sequence of the present protein revealed that the protein was analogous to the rat translocon-associated protein γ subunit (SWISS-PROT Accession No. Q08013). Table 2 shows the comparison of the amino acid sequence between the human protein of the present invention (HP) (SEQ ID NO:6) and the rat translocon-associated protein γ subunit (RN) (SEQ ID NO:7). Therein, the marks of -, *, and . represent a gap, an amino acid residue identical with the protein of the present invention, and an amino acid residue analogous to the protein of the present invention, respectively. The both proteins possessed a homology of 98.4% in the entire region.

genomic libraries or other sources of genomic materials. An "isolated gene" is a gene that has been separated from the adjacent coding sequences, if any, present in the genome of the organism from which the gene was isolated.

TABLE 2

```
HP MAPKGSSKQQSEEDLLLQDFSRNLSAKSSALFFGNAFIVSAIPIWLYWRIWHMDLIQSAV
   *****.******************************************************
RN MAPKGGSKQQSEEDLLLQDFSRNLSAKSSALFFGNAFIVSAIPIWLYWRIWHMDLIQSAV

HP LYSVMTLVSTYLVAFAYKNVKFVLKHKVAQKREDAVSKEVTRKLSEADNRKMSRKEKDER
   ************************************************************
RN LYSVMTLVSTYLVAFAYKNVKFVLKHKVAQKREDAVSKEVTRKLSEADNRKMSRKEKDER

HP ILWKKNEVADYEATTTSIFYNNTLFLVVVIVASFFILKNFNPTVNYILSISASSGLIALL
   ***************************.**************  ****************
RN ILWKKNEVADYEATTFSIFYNNTLFLVLVIVASFFILKNFNPRVNYILSISASSGLIALL

HP STGSK
   *****
RN STGSK
```

Furthermore, the search of the GenBank using the base sequences of the present cDNA has revealed the presence of sequences that possessed a homology of 90% or more (for example, Accession No. AA317439) in EST, but, since they are partial sequences, it can not be judged whether or not any of these sequences codes for the same protein as the protein of the present invention.

The rat translocon-associated protein γ subunit is one of the subunits of the complex that are associated with the localization of endoplasmic reticulum proteins [Hartmann, E. et al., Eur. J. Biochem. 214: 375–381 (1993)]. Accordingly, the present protein is considered to play an important role in the protein retention and folding in the endoplasmic reticulum. The present cDNAs can be utilized for the diagnosis and treatment of diseases that are associated with the function insufficiency of endoplasmic reticulum.

INDUSTRIAL APPLICABILITY

The present invention provides cDNAs coding for human proteins having transmembrane domains and eucaryotic cells expressing said cDNAs. The cDNAs of the present invention can be utilized as probes for the gene diagnosis and gene sources for the gene therapy. Furthermore, the cDNAs can be utilized for large-scale expression of said proteins. Cells, wherein these membrane protein genes are introduced and membrane proteins are expressed in large amounts, can be utilized for detection of the corresponding ligands, screening of novel low-molecular pharmaceuticals, and so on.

The present invention also provides genes corresponding to the polynucleotide sequences disclosed herein. "Corresponding genes" are the regions of the genome that are transcribed to produce the mRNAs from which cDNA polynucleotide sequences are derived and may include contiguous regions of the genome necessary for the regulated expression of such genes. Corresponding genes may therefore include but are not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein. Such methods include the preparation of probes or primers from the disclosed sequence information for identification and/or amplification of genes in appropriate Organisms that have enhanced, reduced, or modified expression of the gene(s) corresponding to the polynucleotide sequences disclosed herein are provided. The desired change in gene expression can be achieved through the use of antisense polynucleotides or ribozymes that bind and/or cleave the mRNA transcribed from the gene (Albert and Morris, 1994, Trends Pharmacol. Sci. 15(7): 250–254; Lavarosky et al., 1997, Biochem. Mol. Med. 62(1): 11–22; and Hampel, 1998, Prog. Nucleic Acid Res. Mol. Biol. 58: 1–39; all of which are incorporated by reference herein). Transgenic animals that have multiple copies of the gene(s) corresponding to the polynucleotide sequences disclosed herein, preferably produced by transformation of cells with genetic constructs that are stably maintained within the transformed cells and their progeny, are provided. Transgenic animals that have modified genetic control regions that increase or reduce gene expression levels, or that change temporal or spatial patterns of gene expression, are also provided (see European Patent No. 0 649 464 B1, incorporated by reference herein). In addition, organisms are provided in which the gene(s) corresponding to the polynucleotide sequences disclosed herein have been partially or completely inactivated, through insertion of extraneous sequences into the corresponding gene(s) or through deletion of all or part of the corresponding gene(s). Partial or complete gene inactivation can be accomplished through insertion, preferably followed by imprecise excision, of transposable elements (Plasterk, 1992, Bioessays 14 (9): 629–633; Zwaal et al., 1993, Proc. Natl. Acad. Sci. USA 90(16): 7431–7435; Clark et al., 1994, Proc. Natl. Acad. Sci. USA 91(2): 719–722; all of which are incorporated by reference herein), or through homologous recombination, preferably detected by positive/negative genetic selection strategies (Mansour et al., 1988, Nature 336: 348–352; U.S. Pat. Nos. 5,464,764; 5,487,992; 5,627,059; 5,631,153; 5,614, 396; 5,616,491; and 5,679,523; all of which are incorporated by reference herein). These organisms with altered gene expression are preferably eukaryotes and more preferably are mammals. Such organisms are useful for the development of non-human models for the study of disorders involving the corresponding gene(s), and for the development of assay systems for the identification of molecules that interact with the protein product(s) of the corresponding gene(s).

Where the protein of the present invention is membrane-bound (e.g., is a receptor), the present invention also provides for soluble forms of such protein. In such forms part or all of the intracellular and transmembrane domains of the protein are deleted such that the protein is fully secreted from the cell in which it is expressed. The intracellular and transmembrane domains of proteins of the invention can be identified in accordance with known techniques for determination of such domains from sequence information.

Proteins and protein fragments of the present invention include proteins with amino acid sequence lengths that are at least 25% (more preferably at least 50%, and most preferably at least 75%) of the length of a disclosed protein and have at least 60% sequence identity (more preferably, at least 75% identity; most preferably at least 90% or 95% identity) with that disclosed protein, where sequence identity is determined by comparing the amino acid sequences of the proteins when aligned so as to maximize overlap and identity while minimizing sequence gaps. Also included in the present invention are proteins and protein fragments that contain a segment preferably comprising 8 or more (more preferably 20 or more, most preferably 30 or more) contiguous amino acids that shares at least 75% sequence identity (more preferably, at least 85% identity; most preferably at least 95% identity) with any such segment of any of the disclosed proteins.

Species homologs of the disclosed polynucleotides and proteins are also provided by the present invention. As used herein, a "species homologue" is a protein or polynucleotide with a different species of origin from that of a given protein or polynucleotide, but with significant sequence similarity to the given protein or polynucleotide, as determined by those of skill in the art. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encode proteins which are identical, homologous, or related to that encoded by the polynucleotides.

The invention also includes polynucleotides with sequences complementary to those of the polynucleotides disclosed herein.

The present invention also includes polynucleotides capable of hybridizing under reduced stringency conditions, more preferably stringent conditions, and most preferably highly stringent conditions, to polynucleotides described herein. Examples of stringency conditions are shown in the table below: highly stringent conditions are those that are at least as stringent as, for example, conditions A–F; stringent conditions are at least as stringent as, for example, conditions G–L; and reduced stringency conditions are at least as stringent as, for example, conditions M–R.

TABLE 3

| Stringency Condition | Polynucleotide Hybrid | Hybrid Length (bp)‡ | Hybridization Temperature and Buffer† | Wash Temperature and Buffer† |
|---|---|---|---|---|
| A | DNA : DNA | ≥50 | 65° C.; 1 × SSC -or- 42° C.; 1 × SSC, 50% formamide | 65° C.; 0.3 × SSC |
| B | DNA : DNA | <50 | $T_B$*; 1 × SSC | $T_B$*; 1 × SSC |
| C | DNA : RNA | ≥50 | 67° C.; 1 × SSC -or- 45° C.; 1 × SSC, 50% formamide | 67° C.; 0.3 × SSC |
| D | DNA : RNA | <50 | $T_D$*; 1 × SSC | $T_D$*; 1 × SSC |
| E | RNA : RNA | ≥50 | 70° C.; 1 × SSC -or- 50° C.; 1 × SSC, 50% formamide | 70° C.; 0.3 × SSC |
| F | RNA : RNA | <50 | $T_F$*; 1 × SSC | $T_F$*; 1 × SSC |
| G | DNA : DNA | ≥50 | 65° C.; 4 × SSC -or- 42° C.; 4 × SSC, 50% formamide | 65° C.; 1 × SSC |
| H | DNA : DNA | <50 | $T_H$*; 4 × SSC | $T_H$*; 4 × SSC |
| I | DNA : RNA | ≥50 | 67° C.; 4 × SSC -or- 45° C.; 4 × SSC, 50% formamide | 67° C.; 1 × SSC |
| J | DNA : RNA | <50 | $T_J$*; 4 × SSC | $T_J$*; 4 × SSC |
| K | RNA : RNA | ≥50 | 70° C.; 4 × SSC -or- 50° C.; 4 × SSC, 50% formamide | 67° C.; 1 × SSC |
| L | RNA : RNA | <50 | $T_L$*; 2 × SSC | $T_L$*; 2 × SSC |
| M | DNA : DNA | ≥50 | 50° C.; 4 × SSC -or- 40° C.; 6 × SSC, 50% formamide | 50° C.; 2 × SSC |
| N | DNA : DNA | <50 | $T_N$*; 6 × SSC | $T_N$*; 6 × SSC |
| O | DNA : RNA | ≥50 | 55° C.; 4 × SSC -or- 42° C.; 6 × SSC, 50% formamide | 55° C.; 2 × SSC |
| P | DNA : RNA | <50 | $T_P$*; 6 × SSC | $T_P$*; 6 × SSC |
| Q | RNA : RNA | ≥50 | 60° C.; 4 × SSC -or- 45° C.; 6 × SSC, 50% formamide | 60° C.; 2 × SSC |
| R | RNA : RNA | <50 | $T_R$*; 4 × SSC | $T_R$*; 4 × SSC |

‡The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
†SSPE (1 × SSPE is 0.15 M NaCl, 10 mM NaH$_2$PO$_4$, and 1.25 mM EDTA, pH 7.4) can be substituted for SSC (1 × SSC is 0.15 M NaCl and 15 mM sodium citrate) in the hybridization and wash buffers; washes are performed for 15 minutes after hybridization is complete.

TABLE 3-continued

| Stringency Condition | Polynucleotide Hybrid | Hybrid Length (bp)‡ | Hybridization Temperature and Buffer† | Wash Temperature and Buffer† |
|---|---|---|---|---|

*$T_B$-$T_R$: The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$(° C.) = 2(#of A + T bases) + 4(# of G + C bases). For hybrids between 18 and 49 base pairs in length, $T_m$(C) = 81.5 + 16.6($\log_{10}$[Na$^+$]) + 0.41 (%G + C) – (600/N), where N is the number of bases in the hybrid, and [Na$^+$] is the concentration of sodium ions in the hybridization buffer ([Na$^+$] for 1 × SSC = 0.165 M).

Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3–6.4, incorporated herein by reference.

Preferably, each such hybridizing polynucleotide has a length that is at least 25% (more preferably at least 50%, and most preferably at least 75%) of the length of the polynucleotide of the present invention to which it hybridizes, and has at least 60% sequence identity (more preferably, at least 75% identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

What is claimed is:

1. An isolated polynucleotide encoding a human sec61 protein, the polynucleotide comprising the nucleotide sequence set forth in SEQ ID NO:1 or 3.

2. An isolated polynucleotide encoding a humna sec61 protein, the polynucleotide consisting of the nucleotide sequence set forth in SEQ ID NO:1 or 3.

3. An isolated polynucleotide encoding a human translocon-associated protein comprising the amino acid sequence set forth in SEQ ID NO:4.

4. An isolated polynucleotide encoding a human translocon-associated protein, the polynucleotide comprising the nucleotide sequence set forth in SEQ ID NO:2 or 5.

5. An isolated polynucleotide encoding a human translocon-associated protein, the polynucleotide consisting of the nucleotide sequence set forth in SEQ ID NO:2 or 5.

6. An isolated nucleic acid molecule which hybridizes to the nucleic acid molecule of any one of claims 1, 2, 3, 4, or 5 under stringent conditions.

7. An isolated polynucleotide comprising a nucleotide sequence which is complementary to the polynucleotide of any one of claims 1, 2, 3, 4, or 5.

8. An isolated polynucleotide comprising the polynucleotide of any one of claims 1, 2, 3, 4, or 5, and a nucleotide sequence encoding a heterologous polypeptide.

9. An isolated polynucleotide of any one claims 5, 6, 7, 8, or 9, wherein the polynucleotide is operably linked to at least one expression control sequence.

10. A vector comprising the polynucleotide of any one of claims 1, 2, 3, 4, or 5.

11. The vector of claim 10, which is an expression vector.

12. A host cell transfected with the expression vector of claim 11.

* * * * *

UNITED STATES PATENT AND TRADEMARK OFFICE
CERTIFICATE OF CORRECTION

PATENT NO. : 6,500,939 B1
DATED : December 31, 2002
INVENTOR(S) : Seishi Kato et al.

It is certified that error appears in the above-identified patent and that said Letters Patent is hereby corrected as shown below:

Title page,
Item [30], Foreign Application Priority Data, "9/276270" should read -- 9-276270 --.
Item [56], References Cited, OTHER PUBLICATIONS, first, second and third occurrences, "Adams, M.D. et al." "similar to" (second occurrence) should be deleted. "Michael Y. Galperin et al.", "genomics" should read -- genomics, --.

Column 2,
Line 27, "cDNA" should read -- cDNAs --.

Column 6,
Line 3, "effecting" should read -- affecting --;
Line 6, "orfungal" should read -- or fungal --;
Line 8, "causes" should read -- caused --;
Line 24, "to" should be deleted;
Line 31, "to" should read -- to suppress --; and
Line 48, "as ," should read -- as, --.

Column 7,
Line 17, "cad." should read -- Acad. --; and
Line 42, "erythmatosis" should read -- erythematosis --.

Column 12,
Line 24, "endothelium )." should read -- endothelium). --; and
Line 35, "and" should be deleted.

Column 13,
Line 38, "(includinghereditary" should read -- (including hereditary --; and
Line 45, "stroke)." should read -- stroke)). --.

Column 14,
Line 36, "ytokines" should read -- cytokines --;
Line 52, "growth" should read -- growth. --; and
Lines 58, 63, 64 and 65, "effecting" should read -- affecting --.

Column 15,
Line 1, "effecting" should read -- affecting --.

Column 16,
Line 11, "With" should read -- with --.

UNITED STATES PATENT AND TRADEMARK OFFICE
CERTIFICATE OF CORRECTION

PATENT NO. : 6,500,939 B1
DATED : December 31, 2002
INVENTOR(S) : Seishi Kato et al.

It is certified that error appears in the above-identified patent and that said Letters Patent is hereby corrected as shown below:

Column 20,
Line 56, "5,614, 396;" should read -- 5,614,396; --.

Column 37,
Line 37, "humna" should read -- human --; and
Lines 49-51, "Claim 6" should be deleted.

Column 38,
Line 39, "one claims 5, 6, 7, 8," should read -- one of claims 1, 2, 3, 4, or 5, --; and
Line 40, "or 9," should be deleted.

Signed and Sealed this

Twenty-eighth Day of October, 2003

JAMES E. ROGAN
*Director of the United States Patent and Trademark Office*

SEQUENCE LISTING

<160> NUMBER OF SEQ ID NOS: 8

<210> SEQ ID NO 1
<211> LENGTH: 1428
<212> TYPE: DNA
<213> ORGANISM: Homo sapiens

<400> SEQUENCE: 1

```
atggcaatca aatttctgga agtcatcaag cccttctgtg tcatcctgcc ggaaattcag      60
aagccagaga ggaagattca gtttaaggag aaagtgctgt ggaccgctat caccctcttt     120
atcttcttag tgtgctgcca gattcccctg tttgggatca tgtcttcaga ttcagctgac     180
cctttctatt ggatgagagt gattctagcc tctaacagag gcacattgat ggagctaggg     240
atctctccta ttgtcacgtc tggccttata atgcaactct tggctggcgc caagataatt     300
gaagttggtg acaccccaaa agaccgagct ctcttcaacg gagcccaaaa gttatttggc     360
atgatcatta ctatcggcca gtctatcgtg tatgtgatga ccgggatgta tggggaccct     420
tctgaaatgg gtgctggaat ttgcctgcta atcaccattc agctctttgt tgctggctta     480
attgtcctac ttttggatga actcctgcaa aaaggatatg gccttggctc tggtatttct     540
ctcttcattg caactaacat ctgtgaaacc atcgtatgga aggcattcag ccccactact     600
gtcaacactg gccgaggaat ggaatttgaa ggtgctatca tcgcactttt ccatctgctg     660
gccacacgca cagacaaggt ccgagccctt cgggaggcgt tctaccgcca gaatcttccc     720
aacctcatga atctcatcgc caccatcttt gtctttgcag tggtcatcta tttccagggc     780
ttccgagtgg acctgccaat caagtcggcc cgctaccgtg gccagtacaa cacctatccc     840
atcaagctct tctatacgtc caacatcccc atcatcctgc agtctgccct ggtgtccaac     900
ctttatgtca tctcccaaat gctctcagct cgcttcagtg gcaacttgct ggtcagcctg     960
ctgggcacct ggtcggacac gtcttctggg ggcccagcac gtgcttatcc agttggtggc    1020
ctttgctatt acctgtcccc tccagaatct tttggctccg tgttagaaga cccggtccat    1080
gcagttgtat acatagtgtt catgctgggc tcctgtgcat tcttctccaa aacgtggatt    1140
```

```
gaggtctcag gttcctctgc caaagatgtt gcaaagcagc tgaaggagca gcagatggtg    1200
atgagaggcc accgagagac ctccatggtc catgaactca accggtacat ccccacagcc    1260
gcggcctttg gtgggctgtg catcgggggcc ctctcggtcc tggctgactt cctaggcgcc    1320
attgggtctg gaaccgggat cctgctcgca gtcacaatca tctaccagta ctttgagatc    1380
ttcgttaagg agcaaagcga ggttggcagc atgggggccc tgctcttc                 1428

<210> SEQ ID NO 2
<211> LENGTH: 555
<212> TYPE: DNA
<213> ORGANISM: Homo sapiens

<400> SEQUENCE: 2
atggctccta aaggcagctc caaacagcag tctgaggagg acctgctcct gcaggatttc     60
agccgcaatc tctcggccaa gtcctccgcg ctcttcttcg aaacgcgtt catcgtgtct    120 gccatcccca tctggttata ctggcgaata tggcatatgg atcttattca gtctgctgtt    180
ttgtatagtg tgatgaccct agtaagcaca tatttggtag cctttgcata caagaatgtg    240
aaatttgttc tcaagcacaa agtagcacag aagagggagg atgctgtttc caaagaagtg    300
actcgaaaac tttctgaagc tgataataga agatgtctc ggaaggagaa agatgaaaga    360
atcttgtgga agaagaatga agttgctgat tatgaagcta caacattttc catcttctat    420
aacaacactc tgttcctggt cgtggtcatt gttgcttcct tcttcatatt gaagaacttc    480
aaccccacag tgaactacat attgtccata agtgcttcat caggactcat cgccctcctg    540
tctactggct ccaaa                                                     555

<210> SEQ ID NO 3
<211> LENGTH: 3570
<212> TYPE: DNA
<213> ORGANISM: Homo sapiens
<220> FEATURE:
<221> NAME/KEY: CDS
<222> LOCATION: (120)..(1547)
<223> OTHER INFORMATION: At position 3120, n = any nucleotide

<400> SEQUENCE: 3
actgacgtgt ctctcggcgg agctgctgtg cagtggaacg cgctgggccg cgggcagcgt     60
cgcctcacgc ggagcagagc tgagctgaag cgggacccgg agcccgagca gccgccgcc    119 atg gca atc aaa ttt ctg gaa gtc atc aag ccc ttc tgt gtc atc ctg   167
Met Ala Ile Lys Phe Leu Glu Val Ile Lys Pro Phe Cys Val Ile Leu
  1               5                  10                  15 ccg gaa att cag aag cca gag agg aag att cag ttt aag gag aaa gtg   215
Pro Glu Ile Gln Lys Pro Glu Arg Lys Ile Gln Phe Lys Glu Lys Val
             20                  25                  30 ctg tgg acc gct atc acc ctc ttt atc ttc tta gtg tgc tgc cag att   263
Leu Trp Thr Ala Ile Thr Leu Phe Ile Phe Leu Val Cys Cys Gln Ile
         35                  40                  45 ccc ctg ttt ggg atc atg tct tca gat tca gct gac cct ttc tat tgg   311
Pro Leu Phe Gly Ile Met Ser Ser Asp Ser Ala Asp Pro Phe Tyr Trp
     50                  55                  60 atg aga gtg att cta gcc tct aac aga ggc aca ttg atg gag cta ggg   359
Met Arg Val Ile Leu Ala Ser Asn Arg Gly Thr Leu Met Glu Leu Gly
 65                  70                  75                  80 atc tct cct att gtc acg tct ggc ctt ata atg caa ctc ttg gct ggc   407
Ile Ser Pro Ile Val Thr Ser Gly Leu Ile Met Gln Leu Leu Ala Gly
                 85                  90                  95
```

-continued

| | | |
|---|---|---|
| gcc aag ata att gaa gtt ggt gac acc cca aaa gac cga gct ctc ttc<br>Ala Lys Ile Ile Glu Val Gly Asp Thr Pro Lys Asp Arg Ala Leu Phe<br>                100                          105                  110 | 455 |
| aac gga gcc caa aag tta ttt ggc atg atc att act atc ggc cag tct<br>Asn Gly Ala Gln Lys Leu Phe Gly Met Ile Ile Thr Ile Gly Gln Ser<br>           115                          120                          125 | 503 |
| atc gtg tat gtg atg acc ggg atg tat ggg gac cct tct gaa atg ggt<br>Ile Val Tyr Val Met Thr Gly Met Tyr Gly Asp Pro Ser Glu Met Gly<br>130                          135                          140 | 551 |
| gct gga att tgc ctg cta atc acc att cag ctc ttt gtt gct ggc tta<br>Ala Gly Ile Cys Leu Leu Ile Thr Ile Gln Leu Phe Val Ala Gly Leu<br>145                        150                          155                  160 | 599 |
| att gtc cta ctt ttg gat gaa ctc ctg caa aaa gga tat ggc ctt ggc<br>Ile Val Leu Leu Leu Asp Glu Leu Leu Gln Lys Gly Tyr Gly Leu Gly<br>                165                          170                        175 | 647 |
| tct ggt att tct ctc ttc att gca act aac atc tgt gaa acc atc gta<br>Ser Gly Ile Ser Leu Phe Ile Ala Thr Asn Ile Cys Glu Thr Ile Val<br>           180                          185                        190 | 695 |
| tgg aag gca ttc agc ccc act act gtc aac act ggc cga gga atg gaa<br>Trp Lys Ala Phe Ser Pro Thr Thr Val Asn Thr Gly Arg Gly Met Glu<br>                195                          200                        205 | 743 |
| ttt gaa ggt gct atc atc gca ctt ttc cat ctg ctg gcc aca cgc aca<br>Phe Glu Gly Ala Ile Ile Ala Leu Phe His Leu Leu Ala Thr Arg Thr<br>210                          215                          220 | 791 |
| gac aag gtc cga gcc ctt cgg gag gcg ttc tac cgc cag aat ctt ccc<br>Asp Lys Val Arg Ala Leu Arg Glu Ala Phe Tyr Arg Gln Asn Leu Pro<br>225                        230                          235                  240 | 839 |
| aac ctc atg aat ctc atc gcc acc atc ttt gtc ttt gca gtg gtc atc<br>Asn Leu Met Asn Leu Ile Ala Thr Ile Phe Val Phe Ala Val Val Ile<br>                      245                          250                        255 | 887 |
| tat ttc cag ggc ttc cga gtg gac ctg cca atc aag tcg gcc cgc tac<br>Tyr Phe Gln Gly Phe Arg Val Asp Leu Pro Ile Lys Ser Ala Arg Tyr<br>                    260                          265                        270 | 935 |
| cgt ggc cag tac aac acc tat ccc atc aag ctc ttc tat acg tcc aac<br>Arg Gly Gln Tyr Asn Thr Tyr Pro Ile Lys Leu Phe Tyr Thr Ser Asn<br>           275                          280                        285 | 983 |
| atc ccc atc atc ctg cag tct gcc ctg gtg tcc aac ctt tat gtc atc<br>Ile Pro Ile Ile Leu Gln Ser Ala Leu Val Ser Asn Leu Tyr Val Ile<br>290                          295                          300 | 1031 |
| tcc caa atg ctc tca gct cgc ttc agt ggc aac ttg ctg gtc agc ctg<br>Ser Gln Met Leu Ser Ala Arg Phe Ser Gly Asn Leu Leu Val Ser Leu<br>305                          310                          315                  320 | 1079 |
| ctg ggc acc tgg tcg gac acg tct tct ggg ggc cca gca cgt gct tat<br>Leu Gly Thr Trp Ser Asp Thr Ser Ser Gly Gly Pro Ala Arg Ala Tyr<br>                      325                          330                        335 | 1127 |
| cca gtt ggt ggc ctt tgc tat tac ctg tcc cct cca gaa tct ttt ggc<br>Pro Val Gly Gly Leu Cys Tyr Tyr Leu Ser Pro Pro Glu Ser Phe Gly<br>                    340                          345                        350 | 1175 |
| tcc gtg tta gaa gac ccg gtc cat gca gtt gta tac ata gtg ttc atg<br>Ser Val Leu Glu Asp Pro Val His Ala Val Val Tyr Ile Val Phe Met<br>           355                          360                        365 | 1223 |
| ctg ggc tcc tgt gca ttc ttc tcc aaa acg tgg att gag gtc tca ggt<br>Leu Gly Ser Cys Ala Phe Phe Ser Lys Thr Trp Ile Glu Val Ser Gly<br>370                          375                          380 | 1271 |
| tcc tct gcc aaa gat gtt gca aag cag ctg aag gag cag cag atg gtg<br>Ser Ser Ala Lys Asp Val Ala Lys Gln Leu Lys Glu Gln Gln Met Val<br>385                        390                          395                  400 | 1319 |
| atg aga ggc cac cga gag acc tcc atg gtc cat gaa ctc aac cgg tac<br>Met Arg Gly His Arg Glu Thr Ser Met Val His Glu Leu Asn Arg Tyr<br>                    405                          410                        415 | 1367 |

| | |
|---|---|
| atc ccc aca gcc gcg gcc ttt ggt ggg ctg tgc atc ggg gcc ctc tcg<br>Ile Pro Thr Ala Ala Ala Phe Gly Gly Leu Cys Ile Gly Ala Leu Ser<br>420                           425                     430 | 1415 |
| gtc ctg gct gac ttc cta ggc gcc att ggg tct gga acc ggg atc ctg<br>Val Leu Ala Asp Phe Leu Gly Ala Ile Gly Ser Gly Thr Gly Ile Leu<br>           435                     440                     445 | 1463 |
| ctc gca gtc aca atc atc tac cag tac ttt gag atc ttc gtt aag gag<br>Leu Ala Val Thr Ile Ile Tyr Gln Tyr Phe Glu Ile Phe Val Lys Glu<br>450                           455                     460 | 1511 |
| caa agc gag gtt ggc agc atg ggg gcc ctg ctc ttc tgagcccgtc<br>Gln Ser Glu Val Gly Ser Met Gly Ala Leu Leu Phe<br>465                           470                     475 | 1557 |
| tcccggacag gttgaggaag ctgctccaga agcgcctcgg aagggagct ctcatcatgg | 1617 |
| cgcgtgctgc tgcggcatat ggacttttaa taatgttttt gaatttcgta ttctttcatt | 1677 |
| ccactgtgta aagtgctaga cattttccaa tttaaaattt tgcttttat cctggcactg | 1737 |
| gcaaaaagaa ctgtgaaagt gaaattttat tcagccgact gccagagaag tgggaatggt | 1797 |
| ataggattgt ccccaagtgt ccatgtaact tttgttttaa cctttgcacc ttctcagtgc | 1857 |
| tgtatgcggc tgcagccgtc tcacctgttt ccccacaaag ggaatttctc actctggttg | 1917 |
| gaagcacaaa cactgaaatg tctacgtttc attttggcag taggtgtga agctgggagc | 1977 |
| agatcatgta tttcccggag acgtgggacc ttgctggcat gtctccttca caatcaggcg | 2037 |
| tgggaatatc tggcttagga ctgtttctct ctaagacacc attgttttcc cttattttaa | 2097 |
| aagtgatttt tttaaggaca gaacttcttc caaaagagag ggatggcttt cccagaagac | 2157 |
| actcctggcc atctgtggat ttgtctgtgc acctattggc tcttctagct gactcttctg | 2217 |
| gttgggctta gagtctgcct gtttctgcta gctccgtgtt tagtccactt gggtcatcag | 2277 |
| ctctgccaag ctgagcctgg ccaagctagg tggacagacc cttgcagtga tgtccgtttg | 2337 |
| tccagattct gccagtcatc actggacacg tctcctcgca gctgccctag caaggggaga | 2397 |
| cattgtggta gctatcagac atggacagaa actgacttag tgctcacaag cccctacacc | 2457 |
| ttctgggctg aagatcaccc agctgtgttc agaattttct tactgtgctt aggactgcac | 2517 |
| gcaagtgagc agacaccacc gacttccttt ctgcgtcacc agtgtcgtca gcagagagag | 2577 |
| gacagcacag gctcaaggtt ggtagtgaag tcaggttcgg ggtgcatggg ctgtggtggt | 2637 |
| gttgatcagt tgctccagtg tttgaaataa gaagactcat gtttatgtct ggaataagtt | 2697 |
| ctgtttgtgc tgacaggtgg cctaggtcct ggagatgagc accctctctc tggccttag | 2757 |
| ggagtcccct cttaggacag gcactgccca gcagcaaggg cagcagagtt gggtgctaag | 2817 |
| atcctgagga gctcgaggtt tcgagctggc tttagacatt ggtgggacca aggatgtttt | 2877 |
| gcaggatgcc ctgatcctaa gaaggggcc tggggtgcg tgcagcctgt cggggagacc | 2937 |
| ccactctgac agtgggcaca cggcagcctg caaagcacag ggccaccgcc acagcccggc | 2997 |
| agagggcac actctggaga ccttgctggc agtgctagcc aggaaacaga gtgaccaagg | 3057 |
| gacaagaagg gacttgccta aagccaccca gcaactcagc agcagaacca agatgggccc | 3117 |
| agngctcctc catatggccc agggcttacc accctatcac acgtggcctt gtctagaccc | 3177 |
| agtcctgagc aggggagagg ctcttgagac ctgatgccct cctacccaca tggttctccc | 3237 |
| actgccctgt ctgctctgct gctacagagg ggcagggcct cccccagccc acgcttagga | 3297 |
| atgcttggcc tctggcaggc aggcagctgt acccaagctg gtgggcaggg ggctggaagg | 3357 |
| caccaggcct caggaggagc cccatagtcc cgcctgcagc ctgtaaccat cggctgggcc | 3417 |

```
ctgcaaggcc cacactcacg ccctgtgggt gatggtcacg gtgggtgggt gggggctgac    3477
cccagcttcc aggggactgt cactgtggac gccaaaatgg cataactgag ataaggtgaa    3537
taagtgacaa ataaagccag ttttttacaa ggt                                 3570
```

<210> SEQ ID NO 4
<211> LENGTH: 476
<212> TYPE: PRT
<213> ORGANISM: Homo sapiens

<400> SEQUENCE: 4

```
Met Ala Ile Lys Phe Leu Glu Val Ile Lys Pro Phe Cys Val Ile Leu
 1               5                  10                  15

Pro Glu Ile Gln Lys Pro Glu Arg Lys Ile Gln Phe Lys Glu Lys Val
            20                  25                  30

Leu Trp Thr Ala Ile Thr Leu Phe Ile Phe Leu Val Cys Cys Gln Ile
        35                  40                  45

Pro Leu Phe Gly Ile Met Ser Ser Asp Ser Ala Asp Pro Phe Tyr Trp
    50                  55                  60

Met Arg Val Ile Leu Ala Ser Asn Arg Gly Thr Leu Met Glu Leu Gly
65                  70                  75                  80

Ile Ser Pro Ile Val Thr Ser Gly Leu Ile Met Gln Leu Leu Ala Gly
                85                  90                  95

Ala Lys Ile Ile Glu Val Gly Asp Thr Pro Lys Asp Arg Ala Leu Phe
            100                 105                 110

Asn Gly Ala Gln Lys Leu Phe Gly Met Ile Ile Thr Ile Gly Gln Ser
        115                 120                 125

Ile Val Tyr Val Met Thr Gly Met Tyr Gly Asp Pro Ser Glu Met Gly
    130                 135                 140

Ala Gly Ile Cys Leu Leu Ile Thr Ile Gln Leu Phe Val Ala Gly Leu
145                 150                 155                 160

Ile Val Leu Leu Leu Asp Glu Leu Leu Gln Lys Gly Tyr Gly Leu Gly
                165                 170                 175

Ser Gly Ile Ser Leu Phe Ile Ala Thr Asn Ile Cys Glu Thr Ile Val
            180                 185                 190

Trp Lys Ala Phe Ser Pro Thr Thr Val Asn Thr Gly Arg Gly Met Glu
        195                 200                 205

Phe Glu Gly Ala Ile Ile Ala Leu Phe His Leu Leu Ala Thr Arg Thr
    210                 215                 220

Asp Lys Val Arg Ala Leu Arg Glu Ala Phe Tyr Arg Gln Asn Leu Pro
225                 230                 235                 240

Asn Leu Met Asn Leu Ile Ala Thr Ile Phe Val Phe Ala Val Val Ile
                245                 250                 255

Tyr Phe Gln Gly Phe Arg Val Asp Leu Pro Ile Lys Ser Ala Arg Tyr
            260                 265                 270

Arg Gly Gln Tyr Asn Thr Tyr Pro Ile Lys Leu Phe Tyr Thr Ser Asn
        275                 280                 285

Ile Pro Ile Ile Leu Gln Ser Ala Leu Val Ser Asn Leu Tyr Val Ile
    290                 295                 300

Ser Gln Met Leu Ser Ala Arg Phe Ser Gly Asn Leu Leu Val Ser Leu
305                 310                 315                 320

Leu Gly Thr Trp Ser Asp Thr Ser Ser Gly Gly Pro Ala Arg Ala Tyr
                325                 330                 335

Pro Val Gly Gly Leu Cys Tyr Tyr Leu Ser Pro Pro Glu Ser Phe Gly
            340                 345                 350
```

```
Ser Val Leu Glu Asp Pro Val His Ala Val Val Tyr Ile Val Phe Met
        355                 360                 365

Leu Gly Ser Cys Ala Phe Phe Ser Lys Thr Trp Ile Glu Val Ser Gly
        370                 375                 380

Ser Ser Ala Lys Asp Val Ala Lys Gln Leu Lys Glu Gln Gln Met Val
385                 390                 395                 400

Met Arg Gly His Arg Glu Thr Ser Met Val His Glu Leu Asn Arg Tyr
                405                 410                 415

Ile Pro Thr Ala Ala Ala Phe Gly Gly Leu Cys Ile Gly Ala Leu Ser
                420                 425                 430

Val Leu Ala Asp Phe Leu Gly Ala Ile Gly Ser Gly Thr Gly Ile Leu
        435                 440                 445

Leu Ala Val Thr Ile Ile Tyr Gln Tyr Phe Glu Ile Phe Val Lys Glu
        450                 455                 460

Gln Ser Glu Val Gly Ser Met Gly Ala Leu Leu Phe
465                 470                 475
```

```
<210> SEQ ID NO 5
<211> LENGTH: 819
<212> TYPE: DNA
<213> ORGANISM: Homo sapiens
<220> FEATURE:
<221> NAME/KEY: CDS
<222> LOCATION: (66)..(620)

<400> SEQUENCE: 5
gtcaagggcc tttgcccgcc ttggcggccg gctctacgtt ccctgttctc gcctgcagct      60 ccgcc atg gct cct aaa ggc agc tcc aaa cag cag tct gag gag gac ctg    110
      Met Ala Pro Lys Gly Ser Ser Lys Gln Gln Ser Glu Glu Asp Leu
        1               5                  10                  15 ctc ctg cag gat ttc agc cgc aat ctc tcg gcc aag tcc tcc gcg ctc     158
Leu Leu Gln Asp Phe Ser Arg Asn Leu Ser Ala Lys Ser Ser Ala Leu
                 20                  25                  30 ttc ttc gga aac gcg ttc atc gtg tct gcc atc ccc atc tgg tta tac     206
Phe Phe Gly Asn Ala Phe Ile Val Ser Ala Ile Pro Ile Trp Leu Tyr
             35                  40                  45 tgg cga ata tgg cat atg gat ctt att cag tct gct gtt ttg tat agt     254
Trp Arg Ile Trp His Met Asp Leu Ile Gln Ser Ala Val Leu Tyr Ser
         50                  55                  60 gtg atg acc cta gta agc aca tat ttg gta gcc ttt gca tac aag aat     302
Val Met Thr Leu Val Ser Thr Tyr Leu Val Ala Phe Ala Tyr Lys Asn
     65                  70                  75 gtg aaa ttt gtt ctc aag cac aaa gta gca cag aag agg gag gat gct     350
Val Lys Phe Val Leu Lys His Lys Val Ala Gln Lys Arg Glu Asp Ala
 80                  85                  90                  95 gtt tcc aaa gaa gtg act cga aaa ctt tct gaa gct gat aat aga aag     398
Val Ser Lys Glu Val Thr Arg Lys Leu Ser Glu Ala Asp Asn Arg Lys
                100                 105                 110 atg tct cgg aag gag aaa gat gaa aga atc ttg tgg aag aag aat gaa     446
Met Ser Arg Lys Glu Lys Asp Glu Arg Ile Leu Trp Lys Lys Asn Glu
            115                 120                 125 gtt gct gat tat gaa gct aca aca ttt tcc atc ttc tat aac aac act     494
Val Ala Asp Tyr Glu Ala Thr Thr Phe Ser Ile Phe Tyr Asn Asn Thr
        130                 135                 140 ctg ttc ctg gtc gtg gtc att gtt gct tcc ttc ttc ata ttg aag aac     542
Leu Phe Leu Val Val Val Ile Val Ala Ser Phe Phe Ile Leu Lys Asn
    145                 150                 155 ttc aac ccc aca gtg aac tac ata ttg tcc ata agt gct tca tca gga     590
```

```
Phe Asn Pro Thr Val Asn Tyr Ile Leu Ser Ile Ser Ala Ser Ser Gly
160                 165                 170                 175 ctc atc gcc ctc ctg tct act ggc tcc aaa tagaccatgt cagcttcacc      640
Leu Ile Ala Leu Leu Ser Thr Gly Ser Lys
                180                 185 ccctggcttt gtgtctatgg gtggcctgtg gtatatggaa aagtagcagg gtggtcaggg  700
tgggagacac aagatgtttt tatagtctag agcctttaaa aaacccagca gaatgtaatt  760
cagtatttgt ttattggctg ttttttgaca gattgttgaa attaaatgaa ttgaaaggg   819

<210> SEQ ID NO 6
<211> LENGTH: 185
<212> TYPE: PRT
<213> ORGANISM: Homo sapiens

<400> SEQUENCE: 6

Met Ala Pro Lys Gly Ser Ser Lys Gln Gln Ser Glu Glu Asp Leu Leu
1               5                   10                  15

Leu Gln Asp Phe Ser Arg Asn Leu Ser Ala Lys Ser Ser Ala Leu Phe
                20                  25                  30

Phe Gly Asn Ala Phe Ile Val Ser Ala Ile Pro Ile Trp Leu Tyr Trp
            35                  40                  45

Arg Ile Trp His Met Asp Leu Ile Gln Ser Ala Val Leu Tyr Ser Val
    50                  55                  60

Met Thr Leu Val Ser Thr Tyr Leu Val Ala Phe Ala Tyr Lys Asn Val
65                  70                  75                  80

Lys Phe Val Leu Lys His Lys Val Ala Gln Lys Arg Glu Asp Ala Val
                85                  90                  95

Ser Lys Glu Val Thr Arg Lys Leu Ser Glu Ala Asp Asn Arg Lys Met
            100                 105                 110

Ser Arg Lys Glu Lys Asp Glu Arg Ile Leu Trp Lys Lys Asn Glu Val
        115                 120                 125

Ala Asp Tyr Glu Ala Thr Thr Phe Ser Ile Phe Tyr Asn Asn Thr Leu
    130                 135                 140

Phe Leu Val Val Ile Val Ala Ser Phe Phe Ile Leu Lys Asn Phe
145                 150                 155                 160

Asn Pro Thr Val Asn Tyr Ile Leu Ser Ile Ser Ala Ser Ser Gly Leu
                165                 170                 175

Ile Ala Leu Leu Ser Thr Gly Ser Lys
            180                 185

<210> SEQ ID NO 7
<211> LENGTH: 185
<212> TYPE: PRT
<213> ORGANISM: Rattus sp.

<400> SEQUENCE: 7

Met Ala Pro Lys Gly Ser Ser Lys Gln Gln Ser Glu Glu Asp Leu Leu
1               5                   10                  15

Leu Gln Asp Phe Ser Arg Asn Leu Ser Ala Lys Ser Ser Ala Leu Phe
                20                  25                  30

Phe Gly Asn Ala Phe Ile Val Ser Ala Ile Pro Ile Trp Leu Tyr Trp
            35                  40                  45

Arg Ile Trp His Met Asp Leu Ile Gln Ser Ala Val Leu Tyr Ser Val
    50                  55                  60

Met Thr Leu Val Ser Thr Tyr Leu Val Ala Phe Ala Tyr Lys Asn Val
65                  70                  75                  80
```

-continued

```
Lys Phe Val Leu Lys His Lys Val Ala Gln Lys Arg Glu Asp Ala Val
                85                  90                  95

Ser Lys Glu Val Thr Arg Lys Leu Ser Glu Ala Asp Asn Arg Lys Met
            100                 105                 110

Ser Arg Lys Glu Lys Asp Glu Arg Ile Leu Trp Lys Lys Asn Glu Val
        115                 120                 125

Ala Asp Tyr Glu Ala Thr Thr Phe Ser Ile Phe Tyr Asn Asn Thr Leu
    130                 135                 140

Phe Leu Val Val Val Ile Val Ala Ser Phe Phe Ile Leu Lys Asn Phe
145                 150                 155                 160

Asn Pro Thr Val Asn Tyr Ile Leu Ser Ile Ser Ala Ser Ser Gly Leu
                165                 170                 175

Ile Ala Leu Leu Ser Thr Gly Ser Lys
                180                 185

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: chimeric
      DNA-RNA oligonucleotide

<400> SEQUENCE: 8
ggggaattcg agga                                                        14
```